(12) United States Patent
Rodriguez et al.

(10) Patent No.: US 7,744,871 B2
(45) Date of Patent: Jun. 29, 2010

(54) IMMUNOTHERAPEUTIC COMBINATION FOR THE TREATMENT OF TUMORS THAT OVER-EXPRESS RECEPTORS WITH TYROSINE KINASE ACTIVITY

(75) Inventors: Rolando Pérex Rodriguez, Habana (CU); Gisela Maria González Marinello, Ciudad De La Habana (CU); Tania Crobet Ramos, Ciudad Habana (CU); Irene Beausoleil Del Gado, Ciudad De La Habana (CU)

(73) Assignee: Centro De Inmunologia Molecular, Ciudad de la Habana (CU)

( * ) Notice: Subject to any disclaimer, the term of this patent is extended or adjusted under 35 U.S.C. 154(b) by 544 days.

(21) Appl. No.: 11/407,103

(22) Filed: Apr. 20, 2006

(65) Prior Publication Data
US 2006/0188497 A1 Aug. 24, 2006

Related U.S. Application Data

(63) Continuation of application No. 10/005,341, filed on Dec. 7, 2001, now abandoned.

(30) Foreign Application Priority Data
Dec. 8, 2000 (CU) .................................. 287/2000

(51) Int. Cl.
*A61K 39/00* (2006.01)
*A61K 39/385* (2006.01)
*A61K 39/395* (2006.01)

(52) U.S. Cl. .............. 424/130.1; 424/133.1; 424/138.1; 424/141.1; 424/143.1; 424/152.1; 424/155.1; 424/156.1; 424/184.1; 424/192.1; 424/277.1

(58) Field of Classification Search ........................ None
See application file for complete search history.

(56) References Cited

U.S. PATENT DOCUMENTS

| 5,894,018 | A  | * | 4/1999  | Davila et al. ............ | 424/195.11 |
| 6,783,761 | B2 | * | 8/2004  | Grimes et al. ............ | 424/185.1  |
| 2003/0054011 | A1 | * | 3/2003  | Sierra et al. ............. | 424/185.1  |
| 2003/0219380 | A1 | * | 11/2003 | Fong et al. ................ | 424/9.1    |

FOREIGN PATENT DOCUMENTS

WO    WO9851337    * 11/1998

OTHER PUBLICATIONS

Viloria-Petit et al (Cancer Research, 2001, vol. 61, pp. 5090-5101).*
Gonzalez et al (Annals of Oncology, 1998, vol. 9, pp. 431-435).*
Sporn and Roberts ('Autocrine Growth Factors and the Regulation of Tumor Growth', In: Molecular Foundations of Oncology, S. Broder, Ed., 1991, pp. 393-402).*
Disis et al (Clinical Cancer Research, Jun. 1999, vol. 5, pp. 1289-1297).*
Yang et al (Cancer Research, 1999, vol. 59, pp. 1236-1243).*
Crombet et al (Cancer Biotherapy & Radiopharmaceuticals, Feb. 2001, vol. 16, pp. 93-102).*
Kolibaba et al, Biochimica et Biophysica Acta, 1997, vol. 1333, pp. F217-F248.*
Powers et al , Endocrine-Related Cancers, 2000, vol. 7, pp. 165-197.*
Lokker et at (J Biol Chem, 1997, vol. 272, pp. 33037-33044).*
Gill et al (J Biol Chem, 1984, vol. 259, pp. 7755-7760).*
Clark (Protein Engineering of Antibody Molecules for Prophylactic and Therapeutic Applications in Man, 1993, p. 1).*

* cited by examiner

*Primary Examiner*—Karen A Canella
(74) *Attorney, Agent, or Firm*—Rothwell, Figg, Ernst & Manbeck P.C.

(57) ABSTRACT

The present invention is related to the field of immunology and more specifically to cancer immunotherapy, particularly with immunotherapeutic combinations and treatment methods to prevent tumor cell growth and/or to eliminate those cells.

The methods described in the present invention are based on the blockade of receptors with protein kinase activity in tyrosine residues (Receptor Tyrosine Kinases, RTK) and of ligands for those receptors.

Immunotherapeutic combinations are described that cause the blockade of RTK receptors and/or their ligands, by means of a combination of passive and active immunotherapy. The referenced procedures can be applied to patients in different clinical stages with tumors of epithelial origin that over-express those receptors. The combination of active and passive immunotherapy can be simultaneous or sequential independent of whether the therapeutic procedure will be used in patients with advanced disease or as adjuvant therapy.

59 Claims, 8 Drawing Sheets

Figure 9
Patient Initials: CHA
RTP + h-R3 (400 mg)
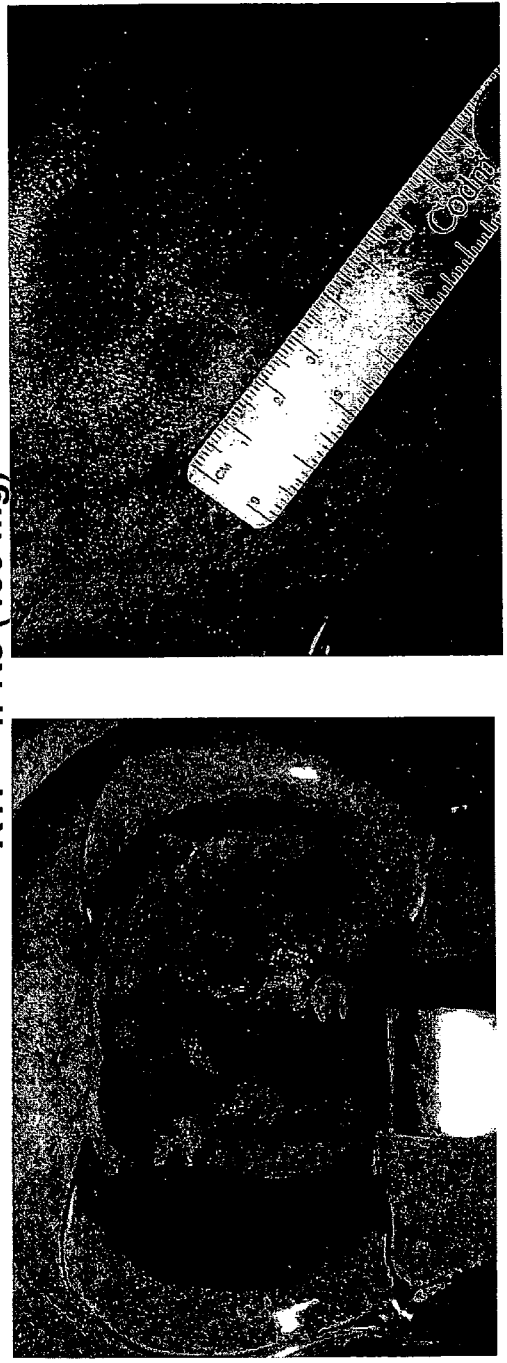
Before (Tonsil tumor and the cervical node)
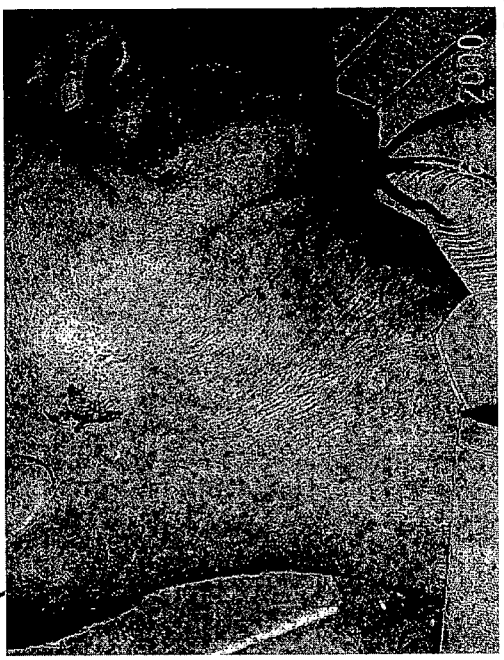
After (Complete remission of the primary tumor and the cervical node)

Time (Days)

IMMUNOTHERAPEUTIC COMBINATION FOR THE TREATMENT OF TUMORS THAT OVER-EXPRESS RECEPTORS WITH TYROSINE KINASE ACTIVITY

The system of the EGF receptor (EGF-R) and its ligands constitutes a molecular complex whose interaction regulates in a specific way cellular growth and its impact has been demonstrated in the uncontrolled growth of tumors of epithelial cell origin. During tumorigenesis the paracrine and autocrine control of EGF-R activation is deregulated, due to growth factor over-production, because of the high rate of synthesis and/or receptor mutations.

The EGF-R is a transmembrane glycoprotein with 1186 amino acids and 170 kD molecular weight that it is broadly expressed in normal tissues. It has been implicated in several stages of embryogenic development.

The binding of its specific ligands, EGF or TGF-alpha, induces receptor dimerization, as well as heterodimerization with other members of the ErbB family, like HER-2 (Cohen BD et al. (1996) J Biol Chem 271:7620-7629). The binding of ligand to receptors releases a cascade of intracellular signals (Ullrich T O and Schlessinger J (1990) Cell 61:203-212) that drives cellular growth and differentiation. Overexpression of the receptor occurs in some types of cancers, mainly of epithelial origin, which has been a target for cancer immunotherapy. Such is the case for breast, bladder, ovary, uterine, colon, lung, brain, prostate and head and neck tumors. EGF-R expression has proven to be an indication of bad prognosis in breast cancer (Pérez R et al. (1984) Breast Cancer and Treatment 4:189-193). While the role of EGFR and its ligands in tumor growth is not yet known, there are suggestions that EGF-R expression in tumor cells induces a mechanism for autocrine stimulation that leads to uncontrolled proliferation of those cells (Schlessinger J et al. (1983) Crit Rev Biochem 14 (2):93-111).

The main ligands of this system are the Epidermal Growth Factor (EGF) and the Transforming Growth Factor alpha type (TGFalpha). There are other ligands belonging to the EGF superfamily, like: amphireguline (AR), crypto-1 (CR1), Heparin Growth Factor, betacellulin, epiregulin, and others.

EGF is a 53 amino acid polypeptide with a molecular weight of 6045 Da, which is mitogenic for cells of epithelial origin. Its action is mainly paracrine through its binding to EGF-R.

TGF alpha is a 50 amino acid polypeptide able to compete with EGF for binding to EGF-R. Anti-EGF antibodies are not able to recognize TGF alpha (Todaro G J et al. (1976), Nature 264:26-31), meaning that both growth factors are two immunologically different entities.

The EGFR—ligand system has been the target of passive immunotherapy (PI) using monoclonal antibodies(Mab) against EGF-R, in native form, associated with drugs, toxins, or radioactive isotopes (Vollmar AM et al. (1987) J Cell Physiol 131:418-425) in tumors with high expression of this receptor. These antibodies have been selected by their capacity to inhibit the binding of EGF to it receptor (neutralizing antibodies). Several clinical trials with Mabs are being carried out and some have shown promising results as it is the case of Phase II clinical trials with the Mab C225 in breast, pancreatic and renal cancer, in addition to Phase III trials in head and neck cancer (Mendelsohn, J et al. (1999) American Society of Clinical Oncology Meeting). Other Phase II clinical trials showing good results have been carried out with the Mab IOR-R3 in lung tumors (Crombet T et al. (2000) Cancer Biotherapy and Biopharmaceutical, manuscript accepted for publication).

Passive immunotherapy with the IOR-R3 Mab (EP586002B1), specific against the EGF-R, has demonstrated that the specific binding of the IOR-R3 to the receptor inhibits EGF/EGF-R binding, with subsequent inhibition of EGFR autophosphorylation. In turn, passive immunotherapy with IOR-R3 inhibited the growth of human tumor cells in nude mice, and it has reduced the rate of tumor growth in some patients in clinical trials. This system has also been target of specific active cancer immunotherapy. One example is the use of a vaccine composed one of the main ligands of EGF-R, EGF, coupled to a carrier protein (U.S. Pat. No. 5,894,018). This vaccine is able to induce a specific antibody response against autologus EGF, to inhibit EGF/EGF-R binding, thus blocking proliferation mechanisms induced by this binding. Pre-clinical studies have shown that mice immunized with autologus EGF coupled to a carrier protein and administered with a useful adjuvant, increases survival of mice transplanted with Ehrlich Ascitic Tumor (EAT) cells (González G et al. (1996), Vaccine Research 5(4):233-243; González G et al (1997) Vaccine Research 6(2):91-100).

Results from a Phase I clinical trial have been reported for a vaccine containing human recombinant EGF, demonstrating the immunogenicity and safety of vaccination (González G et al (1998), Annals of Oncology 9:1-5).

Another example of active specific immunotherapy of cancer in this system is a vaccine composition containing EGF-R, proteoliposomes derived from an external membrane protein complex of *Neisseria meningitidis* and a ganglioside that associate specifically with this receptor forming membrane molecular complexes (Patent deposited in Cuba, priority date 06.12.00).

Likewise, vaccines containing other EGF-R ligands, such as TGF alpha alone or combined with EGF and coupled to a carrier protein, have been developed (Patents Requested in Cuba, priority date 06.12.00).

In the present invention the use of combined immunotherapies is proposed, directed either against receptors with tyrosine kinase activity (RTK) or against their ligands,. This combination has the object of potentiating the observed effect when applying, in an independent way, different forms of immunotherapy described in the state of the art, directed alone against some of the receptor/ligand systems. This potentiation is justified for the combined blockade of both, ligands and receptor, in a treatment method that includes both principles.

DETAILED DESCRIPTION OF THE INVENTION

The present invention is related to immunotherapeutic combinations and treatment methods to inhibit growth of tumor cells to eliminate those cells, based on the blockade of RTK receptors and its ligands. This blockade can be achieved, among other approaches, using combination, simultaneous or sequential, of active immunotherapies (therapeutic vaccines) and passive immunotherapies (Mab) directed to growth factors (i.e.EGF, TGFa) and its receptors (i.e.EGF-R).

The blockade of growth factors or of their receptors causes inhibition of cellular proliferation. In this invention we show that simultaneous blockade of ligands and/or receptors potentiate the inhibition effect on cellular proliferation. This therapeutic concept is of great importance for treatment of malignant tumors, which are fundamentally caused by an increase in the rate of cellular proliferation.

Immunotherapeutic combinations are described that cause the blockade of RTK receptors and/or their ligands, by means of active and passive immunotherapeutical combinations.

The referred procedures can be applied to patients with tumors of epithelial origin that over-express EGF-R, in different clinical stages.

The combination of active and passive immunotherapy can be simultaneous or sequential, independent of the therapeutic procedure used in patients with advanced disease, or as adjuvant therapy.

In cases of advanced disease, the proposed therapeutic combination is passive immunotherapy with Mab that recognizes the RTK receptor and/or Mab that recognizes ligands of this receptor, in combination with an onco-specific therapy of choice, as first line therapy, followed by active immunotherapy using vaccines directed against the ligands of the receptor and/or to the receptor, to maintain the theraputic effect.

In cases of adjuvant therapy the proposed therapeutical combinations are:
1. Passive immunotherapy with Mab that recognize either, the RTK receptor and/or its ligands with active immunotherapy using vaccines directed to the receptor's ligands or to the receptor itself.
2. Passive immunotherapy with Mab that recognize either, the RTK receptor or its ligands as attack therapy, followed by active immunotherapy with vaccines directed to the receptor's ligands or to the receptor itself, as maintenance treatment.

Procedure 1: Therapeutic combination including passive immunotherapy with Mab that recognize the RTK receptor (i.e.EGF-R) and/or the receptor's ligands (i.e.EGF, TGF alpha), followed by active therapy with vaccines directed to the receptor and/or its ligands, to be applied in patients with advanced stage epithelial tumors.

This will be administered to patients with advanced cancer who are not eligible for any other onco-specific therapy.

The first treatment step will be passive immunotherapy with Mab that recognizes the RTK receptor (i.e.EGF-R), with the property of inhibiting this receptor and/or Mab that recognize the receptors ligands (i.e. EGF, TGF alpha). This will be an acute therapy aimed at the goal of tumor remission, and can be used together with the established onco-specific treatment for this stage of disease.

This will be followed by active immunotherapy using vaccines that induce receptor blocking antibodies (i.e.anti-EGF-R) and/or ligand blocking antibodies (i.e.anti-EGF, anti-TGF alpha), with the objective of maintaining disease stabilization for longer periods, to avoid new metastates.

The procedure consists of administration to patients in advanced stages of tumors of epithelial origin, of between 4 and 20 doses, ranging between 100 and 400 mg of a Mab that recognizes and inhibits EGF-R, and/or MAb that recognizes the receptor's ligands. The time between doses will be between 6 to 10 days. The complete treatment can last between 1 to 24 months, concomitant with the established onco-especific therapy. The treatment will continue up to partial or complete tumor regression or up to the point where an adverse reaction occurs that requires treatment cessation.

Between 1 and 4 weeks after this treatment, immunization schedules will be initiated with vaccines directed against EGF-R or its ligands (i.e.EGF , TGFalpha) coupled to a carrier protein (i.e.P64K *Neisseria meningitides* recombinant protein) and administered in an adequate adjuvant i.e alum (between 1 and 2 mg/dose) or Montanide ISA 51 (between 0.6 and 1.2 ml/dose). Each dose contains between 50 and 800 ug of active ingredient (receptor or ligand) coupled to the carrier protein, in a final volume of between 0.6 and 5 mL. The immunization schedule is 5 to 8 initial immunizations for response induction, given every 7 to 14 days. Immunizations can be preceded by administration of cyclophosphamide, between 100 and 500 mg/m$^2$ of body weight, administered 2 to 4 days before the 1$^{rst}$ immunization. Vaccines can be formulated in any other vaccine vehicle (i.e.liposomes, DNA vaccines, viral vectors).

Vaccines can be formulated as independent products or as a unique vaccine formulation. In this period, blood will be extracted from patients in order to measure biochemical blood markers and specific antibody titers against the ligand or receptor to which the vaccine is directed. Extractions will be done weekly or monthly.

Subsequently, re-immunizations will be done if antibody titers decrease, every 1 to 4 months for a period of 1 to 2 years.

Procedure 2: Immunotherapeutic combination including passive immunotherapy with Mab that recognizes a RTK receptor (i.e.EGF-R) and/or it ligands (i.e. EGF, TGF alpha) together with active immunotherapy with vaccines directed against the receptor and/or its ligands, as adjuvant treatment.

Passive treatment with Mab recognizing a RTK receptor (i.e.EGF-R) inhibiting its activity and/or Mab recognizing receptor's ligands (i.e.EGF, TGF alpha), together with an active treatment with vaccines that induces an antibody response that blocks the receptor and/or its ligands, will be administered to patients immediately after diagnosis and/or surgical treatment.

Those treatments, administered together, will have a synergistic effect, enabling a higher percentage of regression and/or clinical disease stabilization.

Patients with tumors of epithelial origin are amenable to this treatment, that consists of between 4 to 20 doses, ranging between 100 and 400 mg, of Mab recognizing and inhibiting RTK receptors and/or it ligands. The time between doses will be between 6 to 10 days and the treatment can last between 1 to 24 months. The treatment will continue until partial or complete tumor regression or up to the point where an adverse reaction occurs that requires treatment cessation.

Concomitant immunizations will be administered with vaccines according to the schedule described in procedure #1.

Procedure 3:

Immunotherapeutic combination including passive immunotherapy with Mab recognizing RTK receptors (i.e.EGF-R) and/or its ligands (i.e. EGF, TGF alpha), followed by active immunotherapy with vaccines directed against the receptor and/or it ligands, to be applied as adjuvant therapy.

This will be applied to patients immediately after diagnosis and/or surgical treatment.

The goal of this treatment is to use acute therapy to obtain tumor remission, via initial passive immunotherary with Mab recognizing and inhibiting RTK receptors (i.e.EGF-R) and/or Mab recognizing its ligands (i.e. EGF, TGF alpha).Subsequently, active immunotherapy will be initiated using vaccines inducing blocking antibodies against the receptor (i.e.EGF-R) or it ligands (i.e.EGF, TGF alpha). The aim of the 2$^{nd}$ treatment is to obtain a longer period of freedom from disease, to avoid the appearance of new metastates.

The procedure consists of administration to patients at advanced stages of cancer of epithelial origin, from 4 to 20 doses of between 100 and 400 mg of Mab that recognizes and inhibits the EGF-R and/or its ligands. The time between doses will be between 6 to 10 days and the treatment duration can be between 1 to 24 months. The treatment will continue until partial or complete tumor regression, or until any adverse reaction occurs that requires treatment cessation.

Between 1 to 4 weeks after the end of treatment, immunization schedules will begin with vaccines directed against the EGF-R or some EGF-R ligand (i.e. EGF, TGF alpha), according to the schedule described in procedure #1.

EXAMPLES

Example 1

Immunization Schedule with EGF Vaccine in Cancer Patients, Using Alum as Adjuvant

With the main goal of demonstrating immunogenicity and safety of EGF, a clinical trial was performed in which 10 patients were immunized with an EGF Vaccine (U.S. Pat. No. 5,894,018), using P64K as carrier protein and alum as adjuvant,.

Patient 1.1 (MMG) was included in the trial with a diagnosis of metastasic epidermoid carcinoma of the lung, with progressive disease, and not eligible for any other onco-specific treatment.

The patient was immunized following a schedule of 5 initial dose of the vaccine, containing 50 ug of EGF and 2 mg alum, administered on days 1, 7, 14, 21 and 51.

Blood extraction was performed on days 0, 15, 30, 45, 60 and monthly thereafter for blood biochemical measurements and for EGF-specific antibodies.

Antibody titers were measured by means of an ELISA test, antibody titers being determined as the maximal sera dilution that gives a positive result in the ELISA test. (O.D values equal or higher 2 times the blank).

Re-immunization was performed using the same vaccine dose when a decrease in antibody titers was detected.

Patient MMG developed an anti-EGF antibody response with maximum titers up to 1:8000. The kinetics of the antibody response is shown in FIG. 1.

After the beginning of the vaccination schedule the patient showed clinical and radiological stabilization of disease for 15 months. The patient died 23.2 months after the first vaccination.

Example 2

Immunization Schedule with EGF Vaccine in Cancer Patients, Using Montanide ISA 51 as Adjuvant

With the main goal of demonstrating immunogenicity and safety of EGF using P64K as a carrier protein and Montanide ISA 51 as an adjuvant, a clinical trial was performed in which 10 patients were immunized.

Patient 2.1 (AMG) was included in the trial with a diagnosis of epidermoid carcinoma of the lung, with progressive disease, being ineligible for any other onco-specific treatment.

The patient was immunized according to a schedule of 5 initial doses of the vaccine containing 50 ug of EGF in 0.6 mL total volume, emulsified with 0.6 mL of Montanide ISA 51 immediately before use, and administered on days 1, 7, 14, 21 and 51.

Blood extractions were performed on days 0, 15, 30, 45, 60 and monthly thereafter for blood biochemical measurements and measurement of specific anti-EGF antibodies.

The antibody titers were measured by means of an ELISA test, antibody titers being determined as the maximal sera dilution that gives a positive result in the ELISA test. (O.D values equal or higher 2 times the blank).

Re-immunization was performed using the same vaccine dose when a decrease in antibody titers was detected.

Patient AMG developed an anti-EGF antibody response with maximum titers of up to 1:32000, with a kinetics of response shown in FIG. 2.

After the beginning of the vaccination schedule, the patient showed stabilization of disease for 12 months, at which point clinical and radiological tumor regression was diagnosed.

On the $14^{th}$ month after the beginning of vaccination, a $2^{nd}$ primary tumor appeared. The patient died 18 months after inclusion from a surgical complication of this $2^{nd}$ tumor.

Example 3

Immunization Schedule in Cancer Patients, with EGF Vaccine, Using Alum as Adjuvant and Low Dose Cyclophosphamide Pre-treatment

A clinical trial was carried out in which 10 patients were immunized with the main goal of demonstrating immunogenicity and safety of the EGF Vaccine using P64K. as carrier protein and alum as adjuvant after cyclophosphamide pre-treatment.

Patient 3.1, FNR, was included in the trial with a diagnosis of epidermoid carcinoma of the lung, with progressive disease, being ineligible for any other onco-specific treatment.

The patient was treated with cyclophosphamide (100 $mg/m^2$ of body surface), 3 days before the first immunization of the EGF Vaccine. The vaccination schedule was 5 doses of the vaccine composition, containing 50 ug of EGF and 2 mg of alum, administered on days 1, 7, 14, 21 and 51.

Blood extractions were performed on days 0, 15, 30, 45, 60 and then monthly for blood chemistry and specific anti-EGF antibody determinations.

Antibody titers were measured by means of an ELISA test, antibody titers being determined as the maximal sera dilution that gives a positive result in the ELISA test. (O.D values equal or higher 2 times the blank).

Re-immunization was performed using the same vaccine dose, when a decrease in antibody titers were detected.

The patient developed an anti-EGF antibody response with maximum titers up to 1:8000, as shown in FIG. 4.

After the beginning of the vaccination schedule, the patient showed disease stabilization for 19 months.

Example 4

Immunization Schedule with EGF Vaccine in Cancer Patients, Using Montanide ISA 51 as Adjuvant and Cyclophosphamide Pre-treatment

A clinical trial was carried out in which 10 patients were immunized with the main goal of demonstrating immunogenicity and safety of the EGF Vaccine, using P64K as carrier protein and Montanide ISA 51 as adjuvant after cyclophosphamide pre-treatment.

Patient 4.1, JPG, was included in the trial with a diagnosis of non small cell lung adenocarcinoma, with progressive disease, being ineligible for any other onco-specific treatment.

The patient was treated with cyclophosphamide (100 $mg/m^2$ of body surface), 3 days before the first immunization of the EGF Vaccine. The vaccination schedule was 5 doses of the vaccine composition, containing 50 ug of EGF in 0.6 mL total volume, emulsified with 0.6 mL of Montanide ISA 51 immediately before use, administered on days 1, 7, 14, 21 and 51.

Blood extractions were performed on days 0, 15, 30, 45, 60 and then monthly for blood chemistry and specific anti-EGF antibody determinations.

Antibody titers were measured by means of an ELISA test, antibody titers being determined as the maximal sera dilution that gives a positive result in the ELISA test. (O.D values equal or higher 2 times the blank).

Re-immunization was performed, using the same vaccine dose, when a decrease in antibody titers was detected.

Patient JPG developed an anti-EGF antibody response with maximum titers up to 1:400000, as shown in FIG. 5.

After the beginning of the vaccination schedule the patient showed disease stabilization for 6 months.

Example 5

Inmunogenicity of EGF Vaccination and its Relationship to Disease Stabilization in Patients with Cancer A Phase I trial in 20 patients was performed in which patients were randomized to one of two groups using different adjuvants.

Ten patients at stages III or IV of Non Small Cell Lung cancer (NSCLC), were treated with 5 initial doses of vaccine composition containing 50 ug of EGF and 2 mg of alum, administered on days 1, 7, 14, 21 and 51.

The other 10 patients (NSCLC, stages III or IV), were immunized with 5 doses of the vaccine composition containing 50 ug of EGF, in a total volume of 0.6 mls, emulsified with the same volume (0.6 mL) of Montanide ISA 51.

Antibody titers were measured by means of an ELISA test, with antibody titers determined as the maximal sera dilution that gives a positive result in the ELISA test. (O.D values equal or higher 2 times the blank).

In this trial, 50% of patients developed an anti-EGF antibody response with antibody titers of 1:4000 or higher (Good Antibody Responders, GAR group) and 50% antibody titers below 1:4000 (Bad Antibody Responders, BAR group).

In the GAR group, 87.5% of patients showed clinical and radiological disease stabilization for at least 3 months after the beginning of treatment.

In the BAR group, only 11.1% of patients showed this stabilization profile (Table 1).

These data demonstrate the relationship between anti-EGF antibody levels and tumor stabilization.

CHART 1

Relationship of antibody responses and clinical and radiological disease stabilization.

|  | % of patients | Disease stabilization for at least 3 months after beginning treatment. |
| --- | --- | --- |
| GAR | 50% | 87.5% |
| BAR | 50% | 11.1% |

Example 6

Immunogenicity of EGF Vaccination and Relationship to Survival of Cancer Patient Subjected to this Treatment Forty stage III/IV NSCLC patients were treated, in groups of 10, with the schedules detailed in examples 1, 2, 3 and 4.

They were characterized as GAR and BAR according to criteria exposed in example 6.

Of the total of patients treated with the previously described schedules, 50% turned out to be GAR and 50% BAR.

When survival patterns were compared between GAR and BAR patients, a statistically significant difference was observed, with a mean survival of 9.1 months for GAR and a mean survival of 4.5 months for BAR (p<0.02). This result is showed in FIG. 6.

Example 7

Therapeutic Effect of the Combination of Radiotherapy and Mab IOR-R3

Patient RML, diagnosed with stage IV language base epidermoid carcinoma, was included in the clinical trial using the combination of radiotherapy (RTP) and IOR-R3.

The patient received 200 mg of Mab once a week for 6 weeks. The accumulated dose of Mab was 1200 mg and the total radiation dose was 60 Gy.

When the combination therapy was complete the patient showed complete remission of the primary tumor and its metastases (FIG. 7). This response was maintained for more than 13 months.

Example 8

Therapeutic Effect of the Combination of Radiotherapy and Mab IOR-R3

Patient EPG, diagnosed with stage III tonsil epidermoid carcinoma with cervical adenopathies, was included in the clinical trial using the combination of radiotherapy (RTP) and IOR-R3. The patient received 200 mg of Mab once a week for 6 weeks and a total radiation dose of 64 Gy.

After treatment, this patient showed complete remission of the tumor lesion (FIG. 8).

The response was maintained for more than 13 months.

Example 9

Therapeutic Effect of the Combination of Radiotherapy and Mab IOR-R3

Patient CHA, diagnosed with a stage IV tonsil tumor, with bilateral cervical adenopathies, was included in the clinical trial using a combination of radiotherapy (RTP) and IOR-R3. The patient received 400 mg of Mab once a week for 6 weeks, for an accumulated dose of 2400 mg. Concomitantly, the patient received a total radiation dose of 64 Gy.

When concluding the treatment this patient was in complete remission of the primary tumor and the loco-regional metastasis (FIG. 9). The response was maintained for 12 months.

Example 10

Evaluation, in Nude Mice, of Passive Therapy Using a Combination of Anti-EGF-R Antibody (IOR-R3) and an Anti-EGF-R Ligand Monoclonal (EGF-1)

Evaluation of the anti-tumor effect in relation to the administered doses.

This experiment also simulates the possible effect of combined administration of the anti-EGF-R Mab and an EGF vaccine. The vaccine causes an anti-EGF antibody response with the same effect of passive administration of Mab with that specificity, with the additional advantage that, the achieved antibody response can be maintained over time, as shown in examples 1, 2, 3 and 4 (kinetics of anti-EGF antibody titers in immunized patients)

Seven different groups of athymic mice, with NMRI genetic origin (outbred population), were immunized with:

Group 1: 10 doses of 0.5 mg of the EGF-1 Mab, intraperitoneal route, daily frequency.

Group 2: 10 doses of 1 mg of the EGF-1 Mab, intraperitoneal route, daily frequency.

Group 3: 10 doses of 0.5 mg of the IOR-R3 Mab, intraperitoneal route, daily requency.

Group 4: 10 doses of 1 mg of the IOR-R3 Mab, intraperitoneal route, daily frequency.

Group 5: 10 doses of Phosphate Buffered Saline (PBS), intraperitoneal route, daily frequency (negative control).

Group 6: 10 doses of 0.5 m g EGF-1 Mab combined with 0.5 mg IOR-R3 Mab, intraperitoneal route, daily frequency.

Group 7: 10 doses of 1 m g EGF-1 Mab combined with 1 mg IOR-R3 Mab, intraperitoneal route, daily frequency.

On the day of initiation of treatment with Mabs mice were transplanted with $1 \times 10^6$ H125 human tumor cells. This cell line over-expresses the EGF-R.

Results are shown in FIGS. 10 and 11. The anti-tumor effect was potentiated when both treatments were combined, increasing with increased doses.

Example 11

Schedule of Combined Mab IOR-R3 /EGF Vaccine Treatments in Patients with Advanced Stage Tumors Patient ARP, diagnosed with epidermoid carcinoma of the head and neck, received sequential treatment of Mab IOR-R3 and EGF Vaccine.

The patient received 200 mg of Mab once a week for 6 weeks, in combination with a total of 30 doses of radiotherapy , 5 doses per week for 6 weeks, for an accumulated radiation dose of 60 Gy.

When concluding the treatment, the patient was in complete remission of the primary tumor.

An immunization schedule with the EGF Vaccine began one month after conclusion of the treatment with the Mab. The patient received 5 doses of 50 ug of EGF conjugated to protein P64k, in a total volume of 0.6 mls, emulsified with 0.6 ml of Montanide ISA 51 immediately before use. The immunizations were carried out on days 1, 7, 14, 21 and 51.

The patient remains in the follow-up period.

Example 12

Schedule of Combined Mab IOR-R3 /EGF Vaccine Treatments in Patients with Advanced Stages Tumors Patient MRM, diagnosed with epidermoid carcinoma of the lung, was subjected to surgical intervention. One month after the surgery the patient began a combined treatment of passive immunotherapy with Mab IOR-R3 concomitantly with the EGF vaccine.

FIG. 12 details the schedule of dose intervals. The patient is in follow up.

As can beseen, GAR is associated with a significant increase in survival compared with either BAR or with historical controls.

Figure 1:
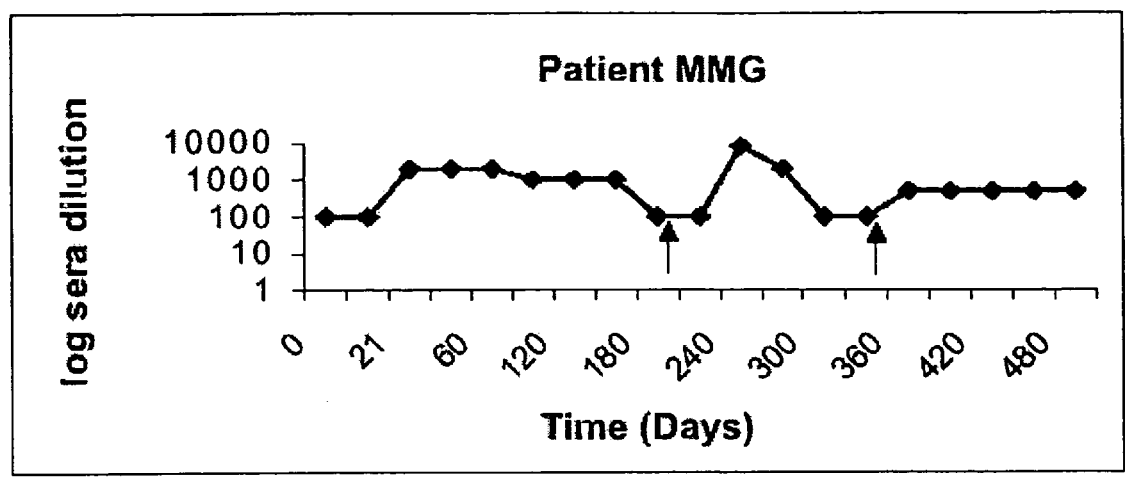
FIG. 1: Kinetics of anti-EGF antibody response in patient MMG, immunized as detailed in example 1. Arrows indicate times of re-immunizations.
Figure 2:
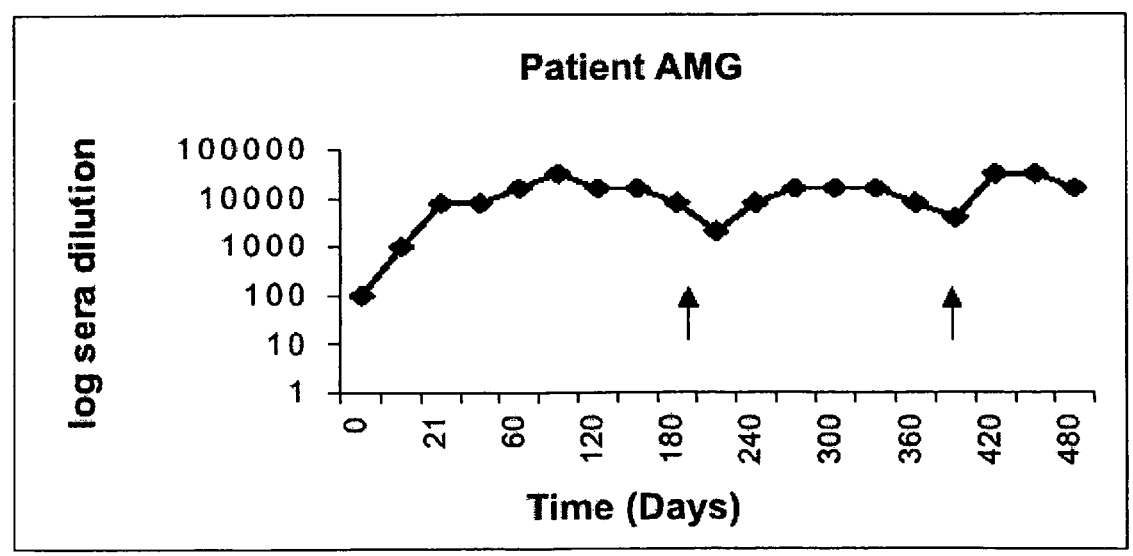
FIG. 2: Kinetics of anti-EGF antibody response in patient AMC, immunized as detailed in example 2. Arrows indicate times of re-immunizations.
Figure 3:
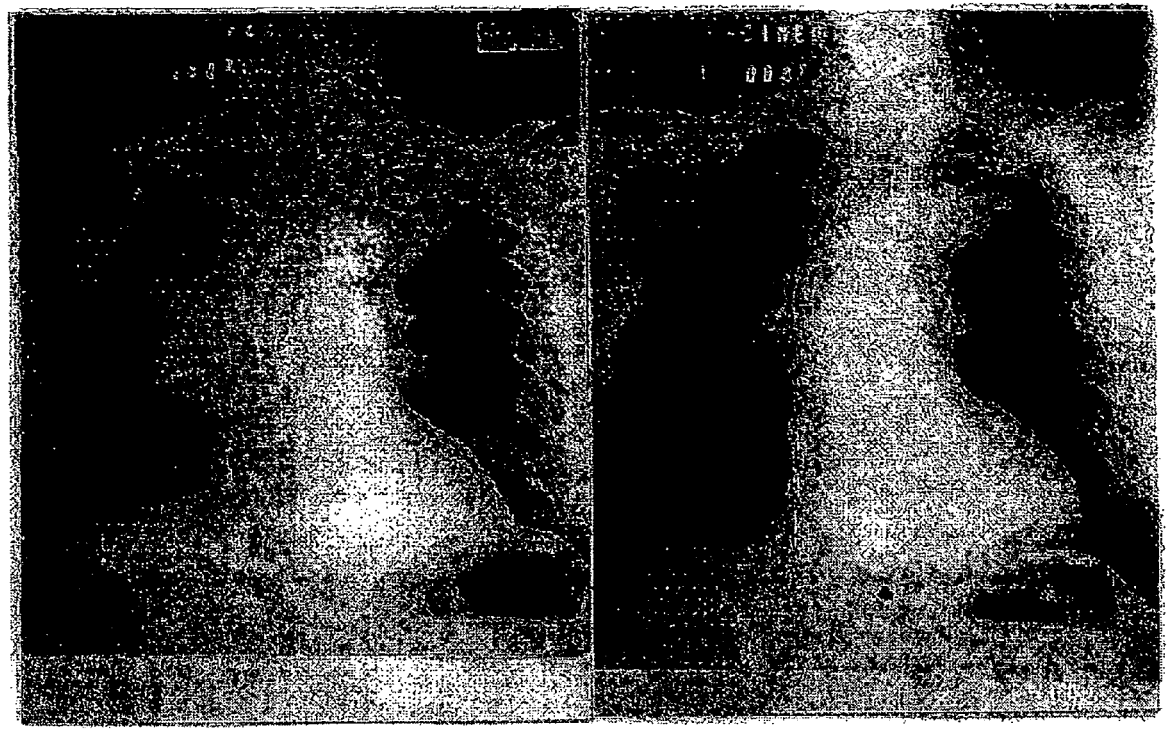
FIG. 3: Tumor regression observed in patient AMC. The tumor mass is seen on the left at the start of treatment. On the right of the figure it can be seen that 12 months after the start of treatment the tumor mass disappeared.
Figure 4:
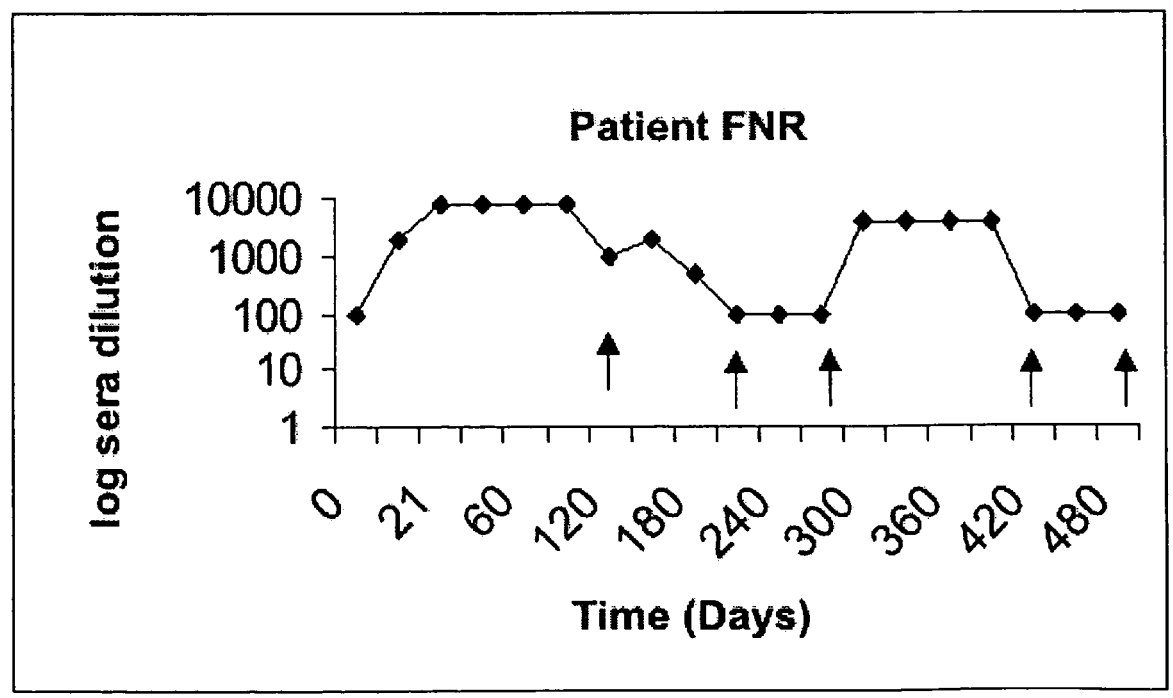
FIG. 4: Kinetics of anti-EGF antibody response in patient FNR, immunized as detailed in example 3. Arrows indicate times of re-immunizations.
Figure 5:
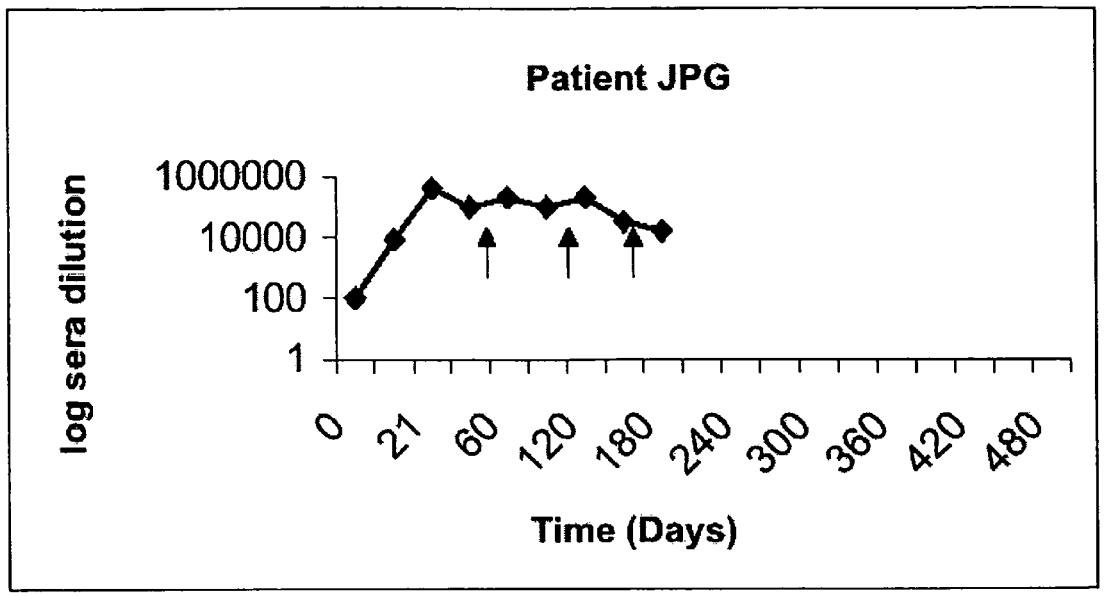
FIG. 5: Kinetics of anti-EGF antibody response in patient JPG, immunized as detailed in example 4. Arrows indicate times of re-immunizations.
Figure 6:
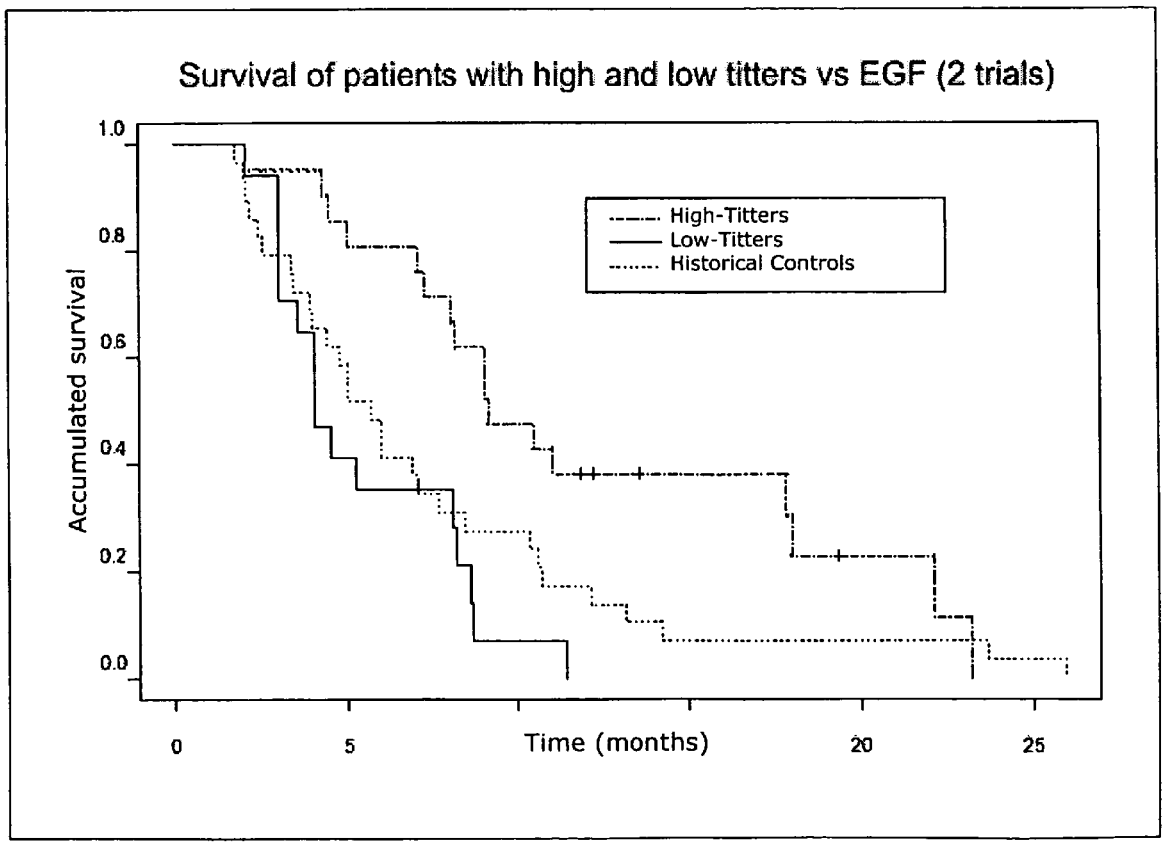
FIG. 6: Kaplan-Maier survival curves of groups of patients with high anti-EGF antibody response (GAR) and with low anti-EGF antibody responses (BAR), as well as that of a historical control group.
Figure 7:
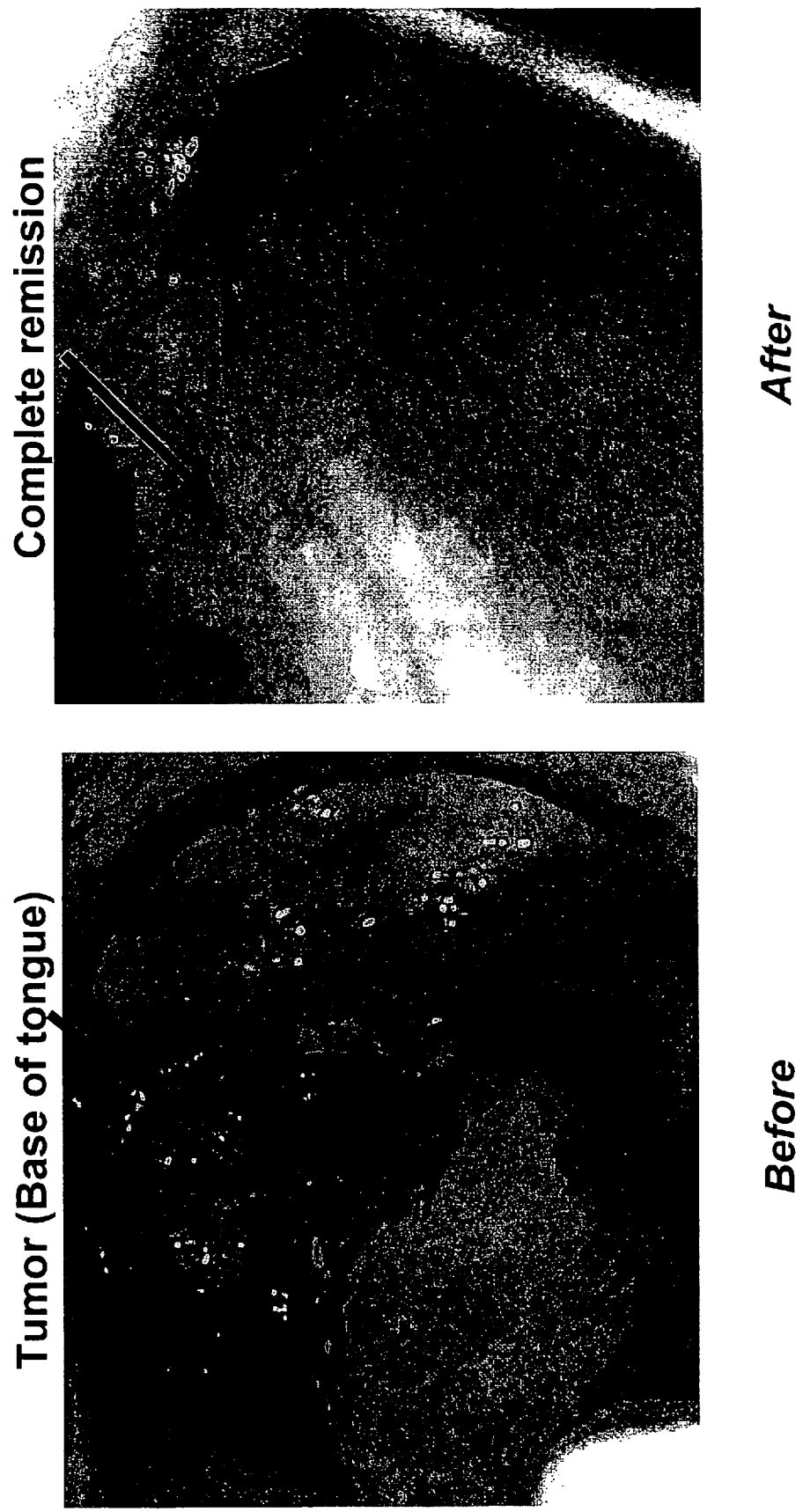

FIG. 7: Graphic demonstration of tumor remission in patient RML, treated as detailed in example 7.

Figure 8:
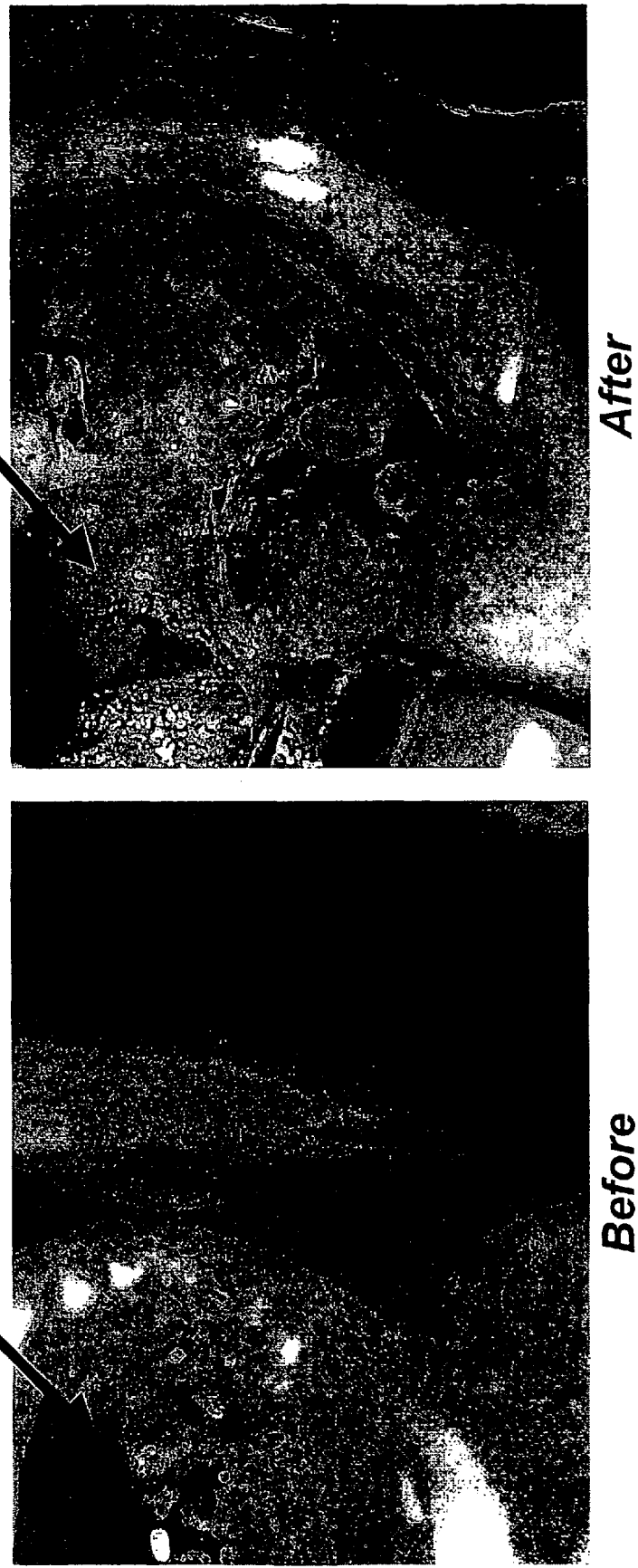

FIG. 8: Graphic demonstration of tumor regression in patient EPG, treated as detailed in example 8.

FIG. 9: Graphic demonstration of the tumor in patient CHA, treated as detailed in example 9.

Figure 10:
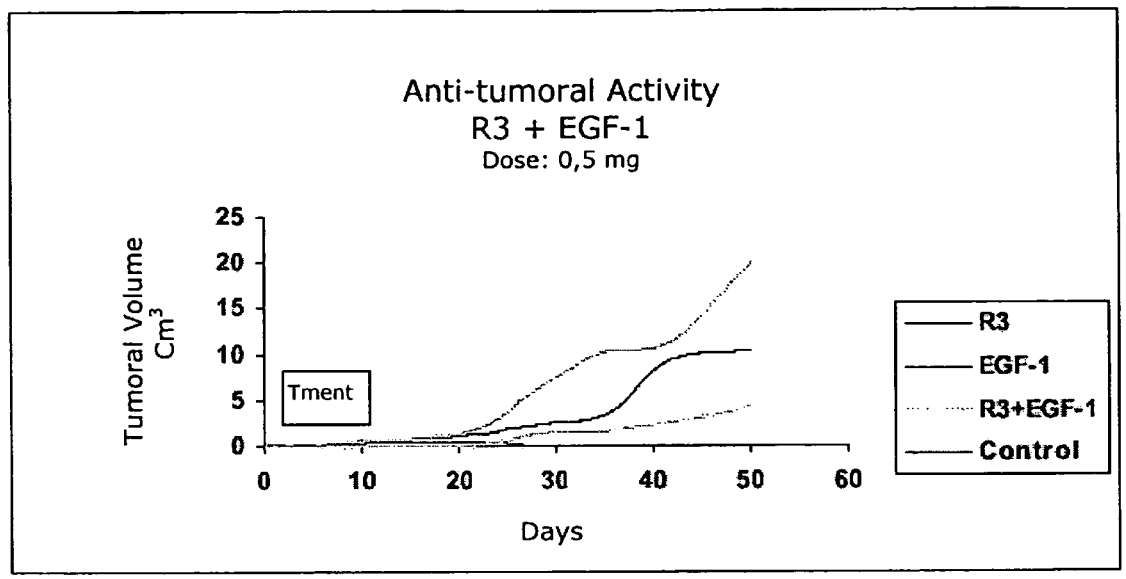

FIG. 10: Groups of mice immunized with 0.5 mg of both Mabs IOR-R3 and EGF-1, and with the combination of 0.5 mg of IOR-R3+0.5 mg of EGF1, as detailed in example 10. A synergistic effect on decreased tumor growth was observed in the group treated with the combination of both Mabs.

Figure 11:
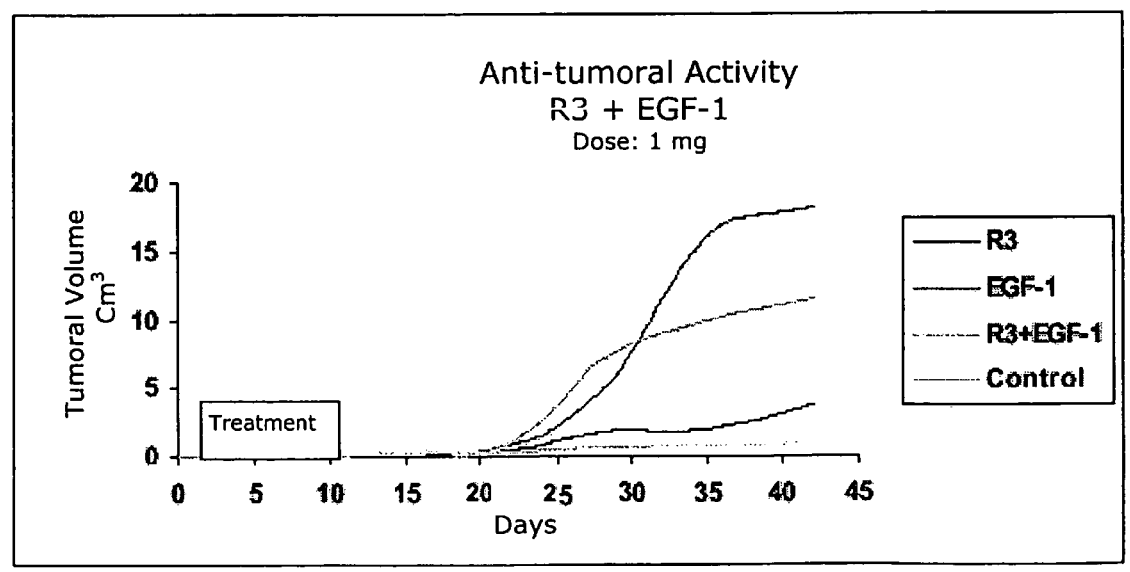

FIG. 11: Groups of mice immunized with 1 mg of both Mabs IOR-R3 and EGF-1, and with the combination of 1 mg of IOR-R3+1 mg of EGF1, as detailed in example 10. A synergistic effect on decreased tumor growth was observed in the group treated with the combination of both Mabs.

Figure 12:
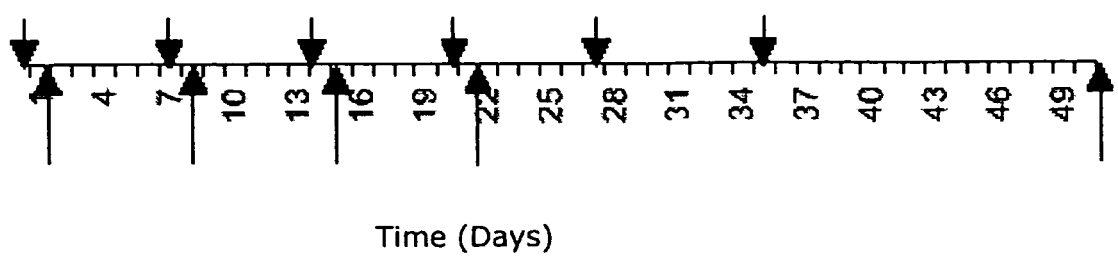

FIG. 12: Combined treatment of Mab IOR-R3 and the EGF Vaccine: p Arrows above the time axis indicate the day of Mab administration (days 1, 7, 14, 21, 28 and 35) and arrows below the time axis indicate the day of immunization with the EGF Vaccine (days 2, 8, 15, 22, and 52).

The invention claimed is:

1. An immunotherapy combination which inhibits the growth and/or proliferation of cells, wherein the growth of said cells is dependent on interaction between a receptor with tyrosine kinase activity (RTK) and its ligand, comprising
   a) an antibody against an EGF receptor, and
   b) a vaccine which induces antibodies against EGF or TGF alpha.

2. The immunotherapy combination according to claim 1, wherein the antibody against the EGF receptor is a monoclonal antibody.

3. The immunotherapy combination according to claim 1, wherein the antibody against the EGF receptor is a humanized antibody.

4. The immunotherapy combination according to claim 3, wherein the humanized antibody has the same binding specificity as IOR R3.

5. The immunotherapy combination according to claim 1, wherein the antibody and the vaccine are in separate containers.

6. The immunotherapy combination according to claim 1, wherein the antibody and the vaccine are in same container.

7. The therapeutic combination according to claim 1, wherein the vaccine induces antibodies against EGF.

8. The therapeutic combination according to claim 7, wherein the vaccine comprises a carrier protein coupled to EGF.

9. The therapeutic combination according to claim 8, wherein the vaccine comprises a conjugate comprising P64K and EGF.

10. The therapeutic combination according to claim 1, wherein the vaccine induces antibodies against TGF-alpha.

11. The therapeutic combination according to claim 10, wherein the vaccine comprises TGF-alpha.

12. The therapeutic combination according to claim 10, wherein the vaccine comprises a carrier protein coupled to TGF-alpha.

13. The therapeutic combination according to claim 12 wherein the vaccine comprises a conjugate comprising proteins P64K and TGF alpha.

14. The immunotherapy combination according to claim 1, wherein said antibody is a Mab, wherein said Mab and said vaccine are in separate formulations, and wherein the combination of said separate formulations induces decreased growth of tumors.

15. The immunotherapy combination according to claim 14, wherein said Mab is directed against the EGF receptor.

16. A method to control growth and/or proliferation of cells or reduce tumor size, wherein the growth of said cells is dependent on interaction between a receptor with tyrosine kinase activity (RTK) and its ligand, comprising administering an immunotherapy combination according to claim 1 to a patient in need of such treatment.

17. The method according to claim 16, wherein said antibody and said vaccine are administered simultaneously.

18. The method according to claim 16, wherein said antibody is administered to said patient first and said vaccine is administered later.

19. The method according to claim 16, wherein said vaccine is administered to said patient first and said antibody is administered later.

20. An immunotherapy treatment combination which inhibits the growth and/or proliferation of cells, wherein the growth of said cells is dependent on interaction between a receptor with tyrosine kinase activity (RTK) and its ligand, comprising
 a) a first agent selected from i) an antibody against an EGF receptor, and ii) a vaccine which induces antibodies against an EGF receptor, wherein the active principle of said vaccine is the EGF receptor,
 b) a second agent selected from i) an antibody against EGF or TGF-alpha, and ii) a vaccine which induces antibodies against EGF or TGF-alpha wherein the active principle of said vaccine is EGF or TGF-alpha.

21. The immunotherapy combination according to claim 20, wherein said first agent is an antibody against the EGF receptor.

22. The immunotherapy combination according to claim 21, wherein the antibody against the EGF receptor is a monoclonal antibody.

23. The immunotherapy combination according to claim 22, wherein the antibody against the EGF receptor is a humanized antibody.

24. The immunotherapy combination according to claim 23, wherein the antibody against the EGF receptor has the same binding specificity as IOR R3.

25. The immunotherapy combination according to claim 20, wherein the first agent is a vaccine whose active principle is an EGF receptor.

26. The immunotherapy combination according to claim 20, wherein the second agent is an antibody against EGF.

27. The immunotherapy combination according to claim 20, wherein the second agent is an antibody against TGF-alpha.

28. The immunotherapy combination according to claim 20, wherein the second agent is a vaccine whose active principle is EGF or TGF-alpha.

29. The immunotherapy combination according to claim 28, wherein the vaccine contains EGF as active principle.

30. The therapeutic combination according to claim 29, wherein the vaccine comprises a carrier protein coupled to EGF.

31. The immunotherapy combination according to claim 29, wherein the vaccine contains conjugated proteins p64K and EGF as active principle.

32. An immunotherapy combination according to claim 28, wherein the vaccine contains TGF-alpha as active principle.

33. The immunotherapy combination according to claim 32, wherein the vaccine comprises a carrier protein coupled to TGF-alpha.

34. An immunotherapy combination according to claim 33 wherein the vaccine contains conjugated proteins P64K and TGF alpha as active principle.

35. The immunotherapy treatment combination according to claim 20, wherein said first agent is a vaccine which induces antibodies against an EGF receptor, wherein the active principle of said vaccine is the EGF receptor, and said second agent is a vaccine which induces antibodies against EGF or TGF-alpha wherein the active principle of said vaccine is EGF or TGF-alpha.

36. A method to control growth and/or proliferation of cells or reduce tumor size, wherein the growth of said cells is dependent on interaction between a receptor with tyrosine kinase activity (RTK) and its ligand, comprising administering an immunotherapy combination according to claim 20 to a patient in need of such treatment.

37. The method according to claim 36, wherein said antibody is administered to said patient first and said vaccine is administered later.

38. The method according to claim 36, wherein said vaccine is administered to said patient first and said antibody is administered later.

39. The method according to claim 36, wherein said first agent and said second agent are administered simultaneously.

40. The method according to claim 39, wherein either said first agent or said second agent is a vaccine and the other is an antibody.

41. An immunotherapy treatment combination which inhibits the growth and/or proliferation of cells, wherein the growth of said cells is dependent on interaction between a receptor with tyrosine kinase activity (RTK) and its ligand, comprising a) an antibody against EGF or TGF-alpha, and b) a vaccine which induces antibodies against EGF or TGF-alpha.

42. The immunotherapy combination according to claim 41, wherein the antibody against the EGF is a monoclonal antibody.

43. The immunotherapy combination according to claim 42, wherein the antibody against the EGF is a humanized antibody.

44. A method to control growth and/or proliferation of cells or reduce tumor size, wherein the growth of said cells is dependent on interaction between a receptor with tyrosine kinase activity (RTK) and its ligand, comprising administering an immunotherapy combination according to claim 41 to a patient in need of such treatment.

45. An immunotherapy treatment combination which inhibits the growth and/or proliferation of cells, wherein the growth of said cells is dependent on interaction between a receptor with tyrosine kinase activity (RTK) and its ligand, comprising a) an vaccine which induces antibodies against EGF, and b) a vaccine which induces antibodies against TGF-alpha.

46. A method to control growth and/or proliferation of cells or reduce tumor size, wherein the growth of said cells is dependent on interaction between a receptor with tyrosine kinase activity (RTK) and its ligand, comprising administering an immunotherapy combination according to claim 45 to a patient in need of such treatment.

47. An immunotherapy combination for reducing the size of a tumor, wherein the growth of said tumor is dependent on interaction between a receptor with tyrosine kinase activity (RTK) and its ligand, comprising a) an antibody against an EGF receptor, and b) a vaccine which induces antibodies against an EGF receptor.

48. The therapeutic combination according to claim 47, wherein the vaccine comprises a carrier protein coupled to EGF.

49. The therapeutic combination according to claim 48, wherein the vaccine comprises a conjugate comprising P64K and EGF.

50. The therapeutic combination according to claim 47, wherein the ligand of the RTK receptor is TGF-alpha.

51. The therapeutic combination according to claim 50, wherein the vaccine comprises TGF-alpha.

52. The therapeutic combination according to claim 51, wherein the vaccine comprises a carrier protein coupled to TGF-alpha.

53. The therapeutic combination according to claim 52 where the vaccine comprises a conjugate comprising proteins P64K and TGF alpha.

54. The immunotherapy combination according to claim 47, wherein the antibody against the EGF receptor is a monoclonal antibody.

55. The immunotherapy combination according to claim 47, wherein the antibody and the vaccine are in separate containers.

56. The immunotherapy combination according to claim 47, wherein the antibody and the vaccine are in same container.

57. The immunotherapy combination according to claim 47, wherein the antibody against the EGF receptor is a humanized antibody.

58. The immunotherapy combination according to claim 57, wherein the humanized antibody has the same binding specificity as IOR R3.

59. A method to control growth and/or proliferation of cells or reduce tumor size, wherein the growth of said cells is dependent on interaction between a receptor with tyrosine kinase activity (RTK) and its ligand, comprising administering an immunotherapy combination according to claim 47 to a patient in need of such treatment.

\* \* \* \* \*